United States Patent [19]

Marsh

[11] 4,234,569
[45] Nov. 18, 1980

[54] PRODUCTION OF ALDEHYDE-TREATED ALLERGEN-CONTAINING SUBSTANCES

[75] Inventor: David G. Marsh, Overlea, Md.

[73] Assignee: The Johns Hopkins University, Baltimore, Md.

[21] Appl. No.: 948,409

[22] Filed: Oct. 4, 1978

Related U.S. Application Data

[63] Continuation-in-part of Ser. No. 550,535, Feb. 18, 1975, which is a continuation-in-part of Ser. No. 289,284, Sep. 15, 1972, abandoned, which is a continuation of Ser. No. 865,481, Oct. 10, 1969, abandoned.

[51] Int. Cl.$^3$ .................... A61K 39/35; A61K 39/36; C07G 7/00
[52] U.S. Cl. ................... 424/91; 260/112 R; 260/123.5; 424/85; 424/88; 424/95; 424/177
[58] Field of Search ............ 424/3, 8, 9, 12, 13, 424/85, 88, 91, 92, 93, 177; 260/112 R, 112.5, 123.5

[56] References Cited

U.S. PATENT DOCUMENTS

| 2,019,808 | 11/1935 | Carter | 424/91 |
|---|---|---|---|
| 3,057,775 | 10/1962 | Rendon | 424/3 X |
| 3,135,662 | 6/1964 | Pope | 424/88 |
| 3,794,630 | 2/1974 | Mullan et al. | 424/177 X |
| 3,983,229 | 9/1976 | Relyveld | 424/91 X |
| 3,987,159 | 10/1976 | Spona | 424/75 X |
| 4,070,455 | 1/1978 | Green | 424/91 |

FOREIGN PATENT DOCUMENTS 1257263 12/1971 United Kingdom ............ 424/12

OTHER PUBLICATIONS

Habeeb, The J. of Immunol. vol. 102, 1969 pp. 457–465.
Stull, The J. of Allergy vol. 11, 1940 pp. 439–465.
British J. of Path. vol. 44, 1963 p. 177.
Patterson, et al., J. Immunol. vol. 110, 1973 p. 1402.
Metzger, et al., N.E. J. Med. vol. 295, 1976 p. 1160.
King, Biochem., vol. 1, Jul. 1962, pp. 709–720.
Gross, Chem. Abs. vol. 44, 1963 p. 2323.

*Primary Examiner*—Anna P. Fagelson
*Attorney, Agent, or Firm*—Wills, Green & Mueth

[57] ABSTRACT

This invention relates to a method of production of formaldehyde, and lower saturated aliphatic dialdehyde-treated allergens suitable for the immunotherapy (desensitization) of individuals suffering from allergies of the immediate type in a plurality of steps wherein said formaldehyde and/or said dialdehyde is utilized alone or in combination for the modification of allergen-containing materials. These lower saturated aliphatic mono- and dialdehyde treated allergen-containing materials are useful in ameliorating the symptoms of allergic (atopic) people. Also, they are able to induce formation of blocking antibody in mammals which cross-reacts with the native allergen-containing materials. Reactions with formaldehyde are carried out in a non-phenolic environment in a plurality of steps. The reaction involving combinations of aldehydes can be carried out in a single step.

48 Claims, 8 Drawing Figures

FIG.1
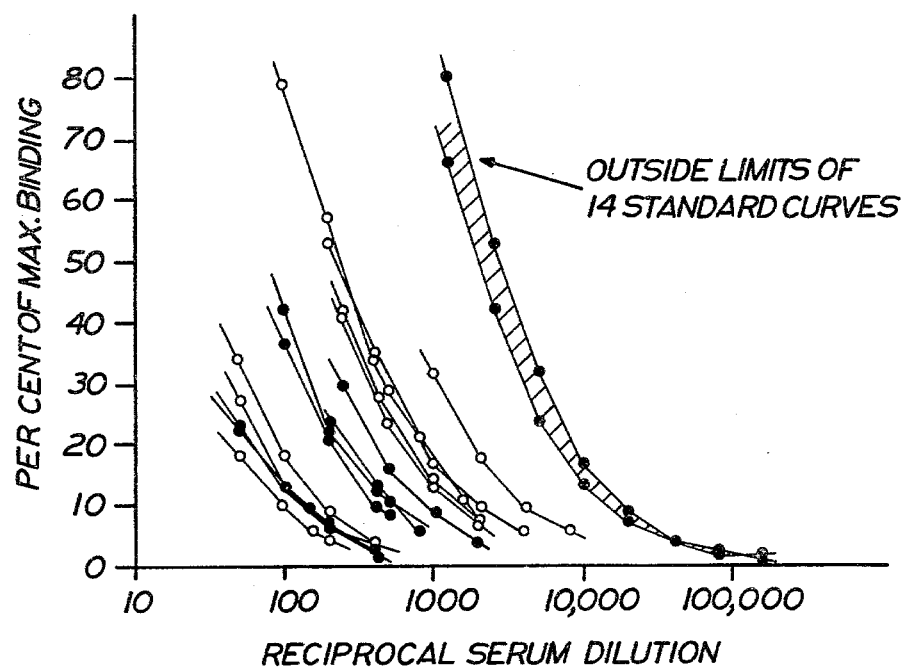
ANTIGEN E BINDING CURVES FOR STANDARD CONTROL SERUM AND ARBITRARILY SELECTED BLEEDS FROM TREATED PATIENTS
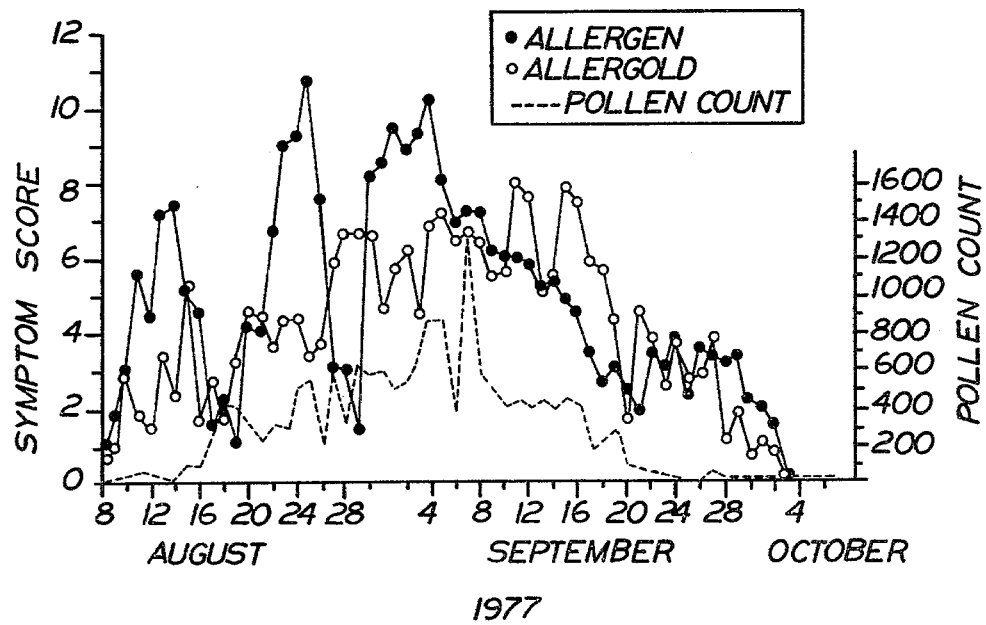
MEAN DAILY SYMPTOM SCORES FOR ALLERGEN- AND ALLERGOID-TREATED PATIENTS TOGETHER WITH RAGWEED POLLEN COUNT (ROTOSLIDE METHOD).
FIG.7

IMMUNOGLOBULIN G ANTIBODY RESPONSES TO ANTIGEN E IN ALLERGEN-ALLERGOID PAIRS NOS. 1 AND 2.

IMMUNOGLOBULIN G ANTIBODY RESPONSES TO ANTIGEN E IN ALLERGEN-ALLERGOID PAIRS NOS. 3 AND 4.

IMMUNOGLOBULIN G ANTIBODY RESPONSES TO ANTIGEN E IN ALLERGEN-ALLERGOID PAIRS NOS. 5 AND 7.

FIG.5 IMMUNOGLOBULIN G ANTIBODY RESPONSES TO ANTIGEN E IN ALLERGEN-ALLERGOID PAIR NO. 6.

CUMULATIVE ANTIGEN DOSE (μg AgE EQUIV.) VERSUS IgG ANTIBODY RESPONSE TO ANTIGEN E IN ALLERGEN-AND ALLERGOID-TREATED PATIENTS. SYMBOLS: ●○ PAIR #1; ●○, PAIR #2; ▲△, PAIR #3; ■□, PAIR #4; ▼▽, PAIR #5; ◆◇, PAIR #7.

DAILY SYMPTOM SCORES (AVERAGED OVER THE ENTIRE RAGWEED SEASON) FOR ALLERGEN-TREATED AND ALLERGOID-TREATED PATIENTS. PATIENTS (A) ON THE 1977 RUSH REGIMEN ARE COMPARED WITH PATIENTS (B) WHO RECEIVED MORE CONVENTIONAL TREATMENT REGIMENS DURING 1973. MEANS FOR EACH GROUP ARE INDICATED BY DASHED LINES.

PRODUCTION OF ALDEHYDE-TREATED ALLERGEN-CONTAINING SUBSTANCES

BACKGROUND OF THE INVENTION

This application relates to a modification of the invention described in co-pending application Ser. No. 550,535 filed Feb. 18, 1975, which is a continuation-in-part of Ser. No. 289,284 filed Sept. 15, 1972, now abandoned and in turn is a continuation of Ser. No. 865,481 filed Oct. 10, 1969, now abandoned. This application is a continuation-in-part of Ser. No. 550,535, the disclosure of said co-pending application being incorporated herein by reference.

As is explained in said co-pending application, patients who suffer from allergies of the immediate type (atopies) have the capacity of make special kinds of allergic antibodies (reagins) upon exposure to certain substances (allergens) toward which they are sensitive. The reagins become strongly attached to certain histamine-containing cells, including the mast cells of the epithelium. Following a subsequent exposure to the sensitizing allergenic material, a physical combination occurs between the allergen(s) and their homologous cell-bound reagins, resulting in allergic manifestations at the sites of reagin-allergen combination. Allergic individuals are also able to produce the so-called "blocking antibodies" of a non-reagin type which are capable of combining with and inactivating the allergen, generally without any undesirable side reactions. Reaginic activity has been attributed to immunoglobulin E (IgE) and "blocking" activity to IgG in the serum and IgA and IgG in secretions.

It has long been the clinical practice to inject an allergic patient with gradually increasing doses of aqueous extracts containing the allergenic material(s) toward which the patient is sensitive. Historically, the basis for this treatment has primarily been to build up the concentration of protective blocking antibody in the serum (and other body fluids) to a level where it could effectively compete with the cell-bound reagin for allergen which enters the body, thereby inhibiting the allergic reactions. It is now thought that the mechanism(s) whereby immunotherapy leads to amelioration of allergic symptons is (are) more complex. In certain cases, this therapy has also been found to suppress the production of reagins and to decrease the cellular responsiveness toward the injected allergens.

Whatever the precise mechanism(s) whereby immunotherapy results in symptomatic relief, several studies have shown that it is essential to inject an adequately large dosage of extract into the patient in order that the treatment may be effective. Unfortunately, in conventional treatment the immunizing doses of the allergenic extract must be increased very gradually in order to minimize the risk of a general allergic (anaphylactic) response in the patient.

The main disadvantages of this immunotherapy are: (1) repeated injections are required over many weeks, (2) the treatment is seldom completely effective in alleviating the allergic syndrome, and (3) the risk of general anaphylactic reaction is always present at each stage of the treatment.

The original therapy has, therefore, been modified with the aim of overcoming these disadvantages. More recent forms of treatment include immunizing the patient with either a water-in-oil emulsion of the allergenic extract or by including a slow release adjuvant such as alumina gel or an alginate with an extract of the allergenic material. Such methods have not proved to be entirely satisfactory due to the occurrence of some anaphylactic and some toxic reactions in the patient or to the failure of these preparations to be sufficiently effective clinically.

Several workers have treated allergenic materials chemically or physically in an attempt to reduce substantially their allergenic properties, but retain their capacity to protect an allergic individual against the native allergen. Immunotherapy of allergic individuals using such modified allergens would, it was hoped, retain the desired immunizing properties of the native allergen, including its ability to induce formation of blocking antibody against the native allergen in substantial amounts. Furthermore, the reduced allergenicity of such modified materials would permit the use of greatly increased doses of immunizing material and, thus, greatly enhance the quantity of protective blocking antibody produced.

According to said co-pending application, it was found that employing formaldehyde solution, with or without certain low molecular weight additives, the great majority of allergen-containing substances may be so modified that the said disadvantages of the native allergens with regard to their use in immunotherapy are overcome. (Hereinafter, any allergen-containing substance will be referred to simply as an allergen, although it is recognized that not all components of an allergen-containing substance are necessarily allergenic).

According to British Patent Specification No. 1,282,163, water-insoluble or sparingly water-soluble dialdehyde-modified pollen materials, which are potentially useful in treating allergic patients, have been prepared. According to Patterson et al. (*J. Immunol.* 110: 1402, 1973), water-soluble glutaraldehyde-modified ragweed polymers have been prepared. A subsequent study of glutaraldehyde-modified ragweed antigen E (Metzger et al., *New Eng. J. Med.* 295: 1160, 1976) suggests that this material may be useful in therapy of ragweed-allergic subjects.

Applicant has now discovered that improved formaldehyde and lower saturated aliphatic dialdehyde-treated allergen-containing materials can be obtained by reaction in a first step at low temperature, usually around 10° C., with formaldehyde and/or a dialdehyde, followed preferably, but not necessarily, by a second step at an elevated temperature, usually around 32° C., followed, if required, by further steps at similarly elevated temperatures, wherein amines, amino acids and related compounds may be optionally utilized at any one or combination of steps, and wherein formaldehyde or any of said dialdehydes can be utilized in any combination or sequence in the step-wise process. In referring to the new aldehyde-treated allergens, the term "aldehyde-modified" will be restricted to describing modified allergens wherein inter- or intra-molecular cross-linkages have been established between or within the allergen molecules themselves and between allergen and other reactive molecules present in the reaction mixture.

U.S. Pat. No. 3,135,662 and the related article in *Brit. J. Exp. Path,* 44, 177 (1963) describing the toxoiding of purified diphtheria toxin with formalin in sodium bicarbonate (0.5% w/v) at pH 7.5. Toxoiding proceeded at room temperature and appeared complete in three to four weeks as judged by intracutaneous tests in guinea pigs. Tests for non-toxicity (200 Lf units in a volume of 5.0 ml. injected subcutaneously into guinea pigs) showed late paralysis in all the guinea pigs. Incubation at 30°-32° C. for a further three weeks, after toxoiding appeared to be complete at room temperature, gave a product which, after the free formalin had been eliminated by ultra-filtration, showed no toxicity; but after storage reverted to the toxic state. According to these teachings, the tendency to reversion or reversal is prevented by the addition of various amines and amino acids.

SUMMARY OF THE INVENTION

Briefly, the present invention describes novel formaldehyde and lower saturated aliphatic dialdehyde-treated allergen derivatives produced by allowing allergens to react chemically under mild conditions with the dilute aldehydes including combinations thereof in a plurality of steps, preferably the first step at a low temperature of above the freezing point of the solution, and usually from about 5° to 15° C., and subsequent step(s) at temperature(s) of from about 25° to 40° C., with the proviso that all of the reactions involving formaldehyde are carried out in a non-phenolic environment. The reaction with combinations (mixtures) of aldehydes can be carried out in a single step.

The allergens so treated may be highly purified, partially purified, or crude extracts. The said dialdehydes have the formula

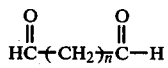

wherein n is from 1 to about 6. As used herein, the term "aldehyde" will refer to the aforestated formaldehyde and lower saturated aliphatic dialdehydes such as glutaraldehyde (n=3), any one of which can be utilized alone or in any combination with any other during the step-wise process.

The term "non-phonolic" is intended to mean that at most only trace amounts of added phenolic compounds are present in the environment of the aldehyde reaction. However, this latter term does not preclude the presence of phenolic hydroxy groups which the allergens per se are known to contain naturally, in most instances, as part of the complex proteinaceous structure.

The procedure of this invention leads to the production of aldehyde-treated allergens of low allergenic reactivity in allergic humans, but which retain the desired immunizing properties of the native (untreated) allergens including, but not limited to, the ability to induce substantial amounts of blocking antibodies, strongly cross-reactive with the native allergens, when injected into humans. Prolonged therapy with such aldehyde-treated allergens has been found to result in a substantial suppression of serum IgE antibodies against the respective allergens. Large therapeutically effective doses of such aldehyde-treated allergens can be administered to allergic humans with a greatly reduced risk of systemic allergic reactions as compared with similar large doses of native allergens, allowing the treating physician to reduce the number of injections of aldehyde-treated allergens relative to those of the native allergens. The aldehyde-treated allergens are also useful for the immunization of other mammals for the purpose of blocking antibody production.

While not bound by any theory, Applicant believes that one major reason why his present aldehyde-modified allergens are superior to those previously described lies in the utilization of a low reaction temperature at the first step. At this low temperature, inter- and intra-molecular cross-linking takes place slowly without adverse thermal or chemical denaturation of critical labile immuno-determinants on the allergens, wherein such adverse reactions are contrary to the need to conserve desired immunizing properties in the aldehyde-modified allergen. The resultant cross-links stabilize the molecule for subsequent reactions at higher temperature, which can be carried out in one or more steps employing the same or a different mono- or dialdehyde. Furthermore, the optimal utilization of more than one dialdehyde creates greater flexibility in the reaction sequence such that aldehyde-modified allergens can be rendered less allergenic by means of reaction with a variety of different aldehydes.

It is an object of this invention to provide new and improved classes of aldehyde-modified allergens.

It is also an object of this invention to provide new techniques for the production of said aldehyde-modified allergens.

These and other objects and advantages of this invention will be apparent from the more detailed description which follows.

DESCRIPTION OF THE PREFERRED EMBODIMENTS

Figure 2:
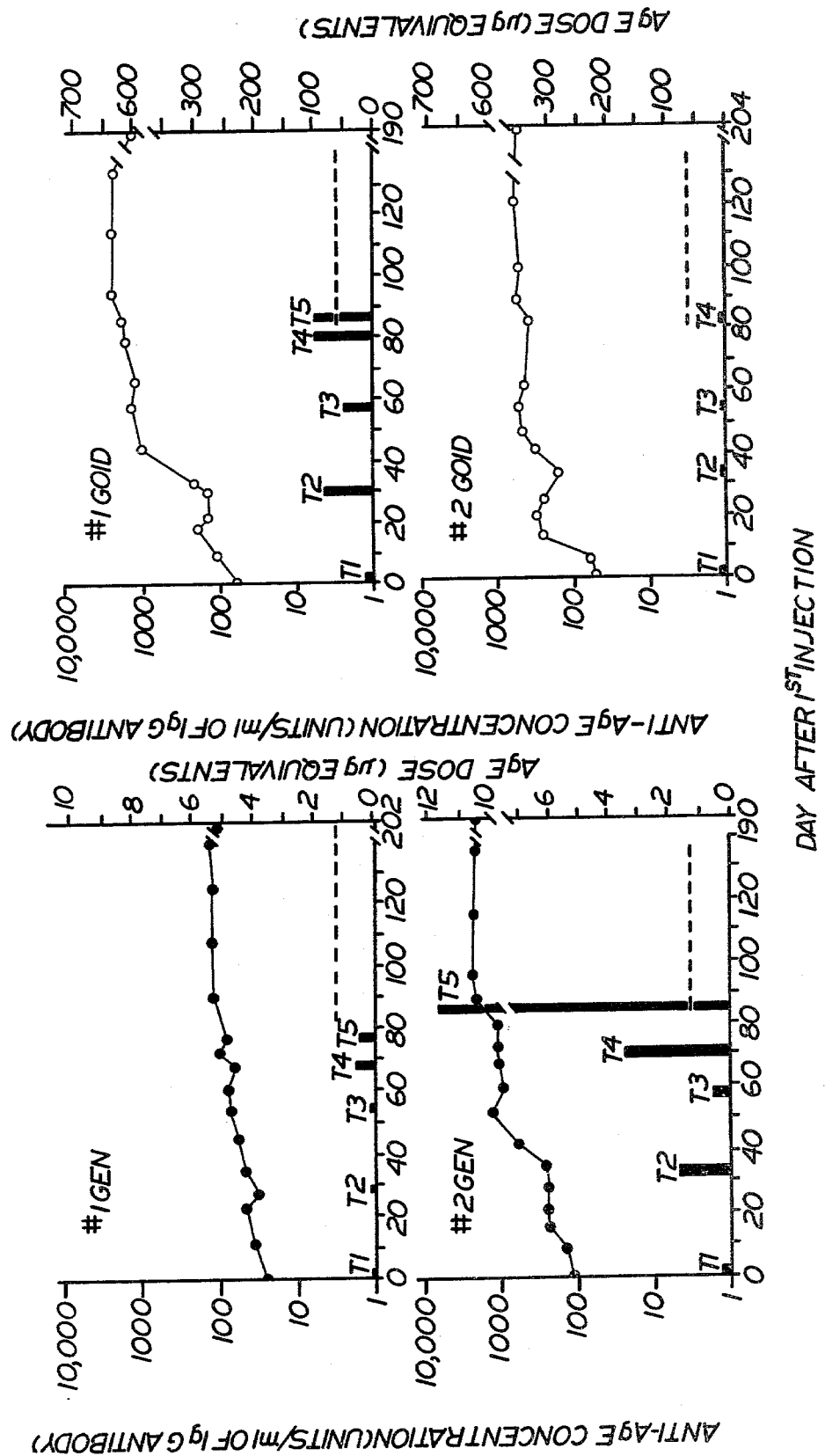

While not bound by any theory, under the reaction conditions in this invention, it is believed that the principal cross-linking reactions involving formaldehyde take place through the establishment of inter- or intra-molecular methylene bridge linkages between amino on the one hand and guanidino, acid amide and certain aromatic groups (especially tyrosyl residues in proteins) on the other. Again, while not bound by any theory, it is also believed that the principal inter- and intra-molecular cross-linking reactions involving the dialdehydes take place between pairs of amino groups. The chemistry of the two types of cross-linking is, therefore, somewhat different, and the kinetics of the dialdehyde cross-linking process is appreciably more rapid than that involving formaldehyde. It should further be noted that when an appropriate additive described herein is present in the reaction mixture, extensive inter-molecular cross-linking can take place between allergen molecules and the additive.

Where crude allergens are used, fatty substances and low molecular weight non-allergenic materials in the native substances should preferably, although not necessarily, have been largely removed prior to aldehyde treatment.

Crude allergenic preparations which are particularly suitable for aldehyde treatment may be prepared by defatting the native allergen-containing material with anhydrous peroxide-free diethyl ether or petroleum ether and extracting the defatted materials with an aqueous solution, preferably buffered to about pH 6-8 (e.g., 0.125 M NH$_4$HCO$_3$). Low molecular weight non-allergenic substances, normally present, may then be removed from the extract by dialysis or ultrafiltration through a semipermeable membrane (e.g., Visking tubing, Millipore membrane, Amicon hollow fiber device of an appropriate molecular weight cut-off, usually in the range of about 3,000 to 10,000 daltons and preferably 3,000 to 5,000 daltons), although gel filtrations or a similar process familiar to those skilled in the art, may be used to achieve a similar result; alternatively, the high molecular weight materials may be precipitated without significant irreversible denaturation from the whole extract by a salt or solvent precipitation process, and these high molecular weight materials may be reconstituted from the precipitated materials in the form of an aqueous solution. Purified, or partially purified, allergenic substances may be prepared by any of the procedures commonly used for purification of macromolecules from complex mixtures. Suitable purification processes have been described in the literature for fish allergens, ragweed pollen, rye and timothy grass pollens, fungi, house dust mites and insect venoms, although these are not the only procedures nor the only allergenic materials which may be used in the aldehyde-treatment process.

The present invention is not restricted to any particular allergen-containing material or extract. However, plant pollen allergen-containing materials, particularly those of grasses, trees and weeds important in allergy, may be extracted and treated successfully with the aldehydes in accordance with this invention. Examples of pollens from the grass family (Gramineae) which are useful in the practice of this invention include meadow fescue (*Festuca elatior*), Kentucky blue grass (*Poa pratensis*), and orchard (*Dactylis glomerata*) of the tribe Festuceae; perennial rye grass (*Lolium perenne*) and Italian rye grass (*Lolium multiflorum*) of the tribe Hordeae; timothy (*Phleum pratense*) and red top (*Agrostis palustris*) of the tribe Agrostideae; and sweet vernal (*Anthoxanthum odoratum*) of the tribe Phalarideae. Comparable examples of tree pollens include various species of walnut, such as *Juglans californica*, of birch (e.g. *Betula alba*), of oak (e.g. *Quercus alba*), and of elm (e.g. *Ulmus parvifolia*). Useful weed pollens include short ragweed (*Ambrosia elatior*), tall ragweed (*Ambrosia trifida*), Russian thistle (*Salsola pestifer*), common sage (*Artemisia tridentata*) and English plantain (*Plantago lanceolata*). Other allergenic materials which can be treated include: extracts containing whole bodies and/or excreta and secreta of house dust mites of the genus Dermatophagoides and related genera, such extracts to include crude extracts of house dust; solutions of food allergens (e.g. extracts of nuts, legumes, hens' eggs, etc.); extract of fungi (e.g. Alternaria, Penicillium, Aspergillus, Helminthosporium, yeasts, basidiospores, ascospores, etc.); extracts of plant seeds and fibers (e.g. cotton, castor, etc.); extracts of the whole bodies or venoms of stinging and biting insects (e.g. bees, yellow jackets, hornets, wasps and mosquitoes); and extracts of danders/skin/hair of animals (e.g. cats, dogs, horses, guinea pigs, mice, rabbits, etc.).

Highly purified or partially purified allergens may also be aldehyde-treated, for example, Group I grass pollen allergen, Antigen E of ragweed pollen, partially purified house dust mite extracts and phospholipase-A from bee venom.

The reaction between the crude or highly purified allergenic materials and the aldehyde(s) may be carried out in the presence of a low molecular weight additive. Suitable additives, usually containing less than about eight carbon atoms in addition to any functional groups present, include: aliphatic diamines; guanidines; aliphatic acid amides; aliphatic carboxylic acids containing amino groups, including aliphatic amino acids (monoamino monocarboxylic acids, monoamino dicarboxylic acids, and diamino monocarboxylic acids), aliphatic hydroxyamino acids, and aliphatic diamino dicarboxylic acids; and aliphatic compounds containing combinations of permutations of one or more amino, guanidino and acid amido groups. In addition, a limited number of hydroxy groups may be present in any of the above types of compounds. Species include 1,4-diaminobutane, lysine, orithinine, 1,5-diaminopimelic acid, arginine, adipamide, aspartic acid, serine and alanine. The additive is such that it chemically combines with the pollen components during the process of aldehyde treatment.

For each stage of the process, the concentrations of allergen, aldehyde and any additive present in the reaction mixture and the pH and period of incubation of the reaction mixture which result in optimal conditions of aldehyde treatment are interdependent to some degree. The following conditions are preferred, each condition being subject to maintaining other conditions within appropriate limits in order to achieve a desired aldehyde-treated allergen.

The final concentration of the allergenic materials used for the aldehyde reaction should preferably (1) be such that all components are completely soluble, and (2) be compatible with the concentration of aldehyde and any additive used. In the case of formaldehyde reactions, the solutions should be prepared in an aqueous buffer preferably of about pH 7.4 to 7.6 of a suitable molarity to maintain this pH to about 7.2 to 7.6 during the course of the reaction in order to optimize the occurrence of the desired aldehyde reactions. Concentrations of up to about 12 mg/ml of allergenic materials (based on dry weight of solids/ml) in 0.1 M sodium phosphate buffer at pH 7.5±0.1 usually meet the aforementioned requirements, the selection of the allergen concentration being to some extent dependent on the temperature of incubation and the aldehyde concentration.

In the case of dialdehyde reactions, the pH of reaction solutions should preferably be 7.0 to 8.0 and the allergen concentration 1.0 to 2.0 mg/ml.

The concentration of aldehyde(s) in the reaction mixture should not be so great as to affect adversely the desired immunizing properties of the resultant aldehyde-treated allergen, but should be sufficient to result in extensive destruction of the allergenicity of the native allergen at the particular temperature of the incubation mixture. The resultant reduction in allergenicity is usually in the range of 100 to 10,000-fold following completion of the step-wise process. In addition to the aforesaid factors, preferred aldehyde concentration ranges vary according to the purity of the allergen being treated in that the lower end of the ranges specified below are more appropriately utilized with highly purified materials.

PREFERRED METHODS OF THIS INVENTION

Allergen Preparations

In the case of allergenic extracts, fatty materials are removed from the dried allergen source (pollen, dander, fungus, etc.) by extraction with dry petroleum ether or dry peroxide-free diethylether. The defatted allergenic material is extracted at 0° to 5° C. for about 15 minutes to 4 days with an appropriate buffered solution (e.g., 0.125 M $NH_4HCO_3$) at a pH of 6.0 to 8.0. The length of time depends on the type of extract desired and the nature of the allergen source. Solid material is removed by filtration, centrifugation, or a similar process. Over 90% of low molecular weight (essentially non-allergenic) materials are removed from the extract by dialysis or ultrafiltration across a membrane or hollow fiber device (mol. wt. cut-off 3,000 to 5,000 daltons), or by gel filtration. The allergen solution is brought to a suitable stock concentration in terms of dry weight of solid allergen-containing material per ml (normally 1.5 to 2.0 times that present in Step One—see below), by ultrafiltration and dialysis against, or lyophilization and reconstitution in, a buffer such as 0.1 M sodium phosphate adjusted to pH 7.5±0.1.

Purified or partially purified allergens are also prepared in the same buffer for reactions described below.

Summary of Reaction Conditions

Formaldehyde, Step One:
Allergen concentration, 1.0 to 12.0 mg/ml; formaldehyde concentration, 0.5 to 2.5 M; temperature, 5° to 15° C., preferably about 10° C.; pH 7.2 to 7.6; time 8 to 32 days.

Formaldehyde, Step "n" (where n>1 and generally n=2):
Allergen concentration, 1.0 to 3.0 mg/ml; formaldehyde concentration, 0.36 to 0.5 M; temperature about 25° to 40° C., preferably 30° to 34° C.; pH 7.2 to 7.6; time 16 to 35 days.

Dialdehyde, Step One:
Allergen concentration, 1.0 to 2.0 mg/ml; aldehyde concentration of 0.01 to 0.1 M, preferably about 0.025 M; temperature 5° to 15° C., preferably about 10° C.; pH about 7.0 to 8.0; time 4 to 24 hours, preferably 16 to 20 hours.

Dialdehyde, Step "n" (where n>1 and generally n=2):
Allergen concentration, 1.0 to 2.0 mg/ml; aldehyde concentration, 0.01 to 0.1 M, preferably about 0.025 M; temperature about 25° to 40° C., preferably about 30° C.; pH about 7.0 to 8.0; time 16 to 32 hours, preferably about 24 hours.

At the end of the incubation(s), excess aldehydes are removed by one of the following methods: extensive dialysis with several changes in the dialysate using a cellulose casing such as Visking size 18, extensive membrane dialysis/ultrafiltration utilizing a Millipore, Amicon or equivalent membrane or hollow fiber device with a molecular weight cut-off of about 5,000 to 30,000 daltons, or by gel filtration on an appropriate xerogel such as Sephadex G10 or G25 at about 4° C.

According to this invention, the reaction is carried out in one or more, and preferably two, steps. Where two or more steps are utilized, the first is distinguished from subsequent steps by the different temperatures employed. In the case of multi-step reactions, the reaction sequence may be performed with: (a) formaldehyde in the first and subsequent steps, (b) with a particular dialdehyde in the first and subsequent steps, (c) with formaldehyde in the first and a particular dialdehyde in subsequent steps, (d) with a particular dialdehyde in the first and formaldehyde in subsequent steps, (e) with any combination of formaldehyde and one or more dialdehydes in a series of steps. The preferred combinations are generally the simple cases (a) or (b), but cases (c) and (d) offer the advantage of a combination of different types of chemical reactions using a relatively simple protocol. Reactions of type (e), while often being more complex to perform, offer the combinations of reaction processes which can lead to the greatest reduction of allergenic properties.

Mixtures of formaldehyde and a dialdehyde (normally glutaraldehyde) may be utilized in a series of steps (usually two). This approach eliminates removal of the aldehyde after the first step before adding the second aldehyde. Since the dialdehyde reaction is essentially complete within about 20 hours, the mixture can then be transferred to the second step to allow more extensive reaction with formaldehyde to take place. The allergen concentration is maintained throughout at about 1.0 to 2.5 mg/ml, formaldehyde at 0.36 to 0.5 M and dialdehyde at about 0.025 M, at a pH of 7.2 to 7.6. The first step is for 4 to 24 hours (preferably 16 to 20 hours) at 5° to 15° C. (preferably about 10° C.) and the second step for 16 to 32 days at 30° to 34° C.

In the first step, the reaction is conducted at a temperature above the freezing point of the solution (the most efficacious range being about 5° to 15° C.) and preferably at about 10° C. The subsequent step(s) is/are carried out at about 25° C. to 40° C. and preferably at 30° to 34° C. The adherence to this sequence of temperatures has been found to increase substantially the efficacy of the final product for the immunization of allergic individuals.

In the case of the preferred two-step process, the first step at the lower temperature is generally carried out for a time period of about 8 to 32 days in the case of formaldehyde, and about 20 hours in the case of the dialdehydes, although in the latter case shorter incubation periods of 4 hours may be used. The duration of the second step is generally about 14 to 35 days for formaldehyde, and about 24 hours for the dialdehydes.

This invention is applicable to formaldehyde, to all lower saturated aliphatic dialdehydes, particularly glutaraldehyde, and dialdehydes of the general formula

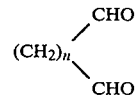

where n≃1 to 6 and their branched-chain isomers and precursors, and to mixtures thereof.

The aldehyde-treated allergens, prepared as described above, are suitable immunotherapeutic agents for mammals, including allergic humans. An adjuvant such as an alum or an alginate can be incorporated into the desired immunizing preparation to enhance the immunogenic efficacy. The aldehyde-treated allergens can be be used in diagnostic testing both before and during immunotherapy of allergic humans.

The aldehyde-treated allergens of this invention can be administered to mammals in a conventional manner such as intradermally, subcutaneously or intramuscularly. In addition, the low allergenicity of these materials permits administration in the form of an aerosol spray to the nose and/or mouth to achieve immunization transmucosally.

This invention is illustrated, but not limited, by the following examples:

EXAMPLE 1

The following pollens were used: (1) short ragweed (*Ambrosia elatior*), and (2) mixed grass comprising 30% orchard (*Dactylis glomerata*), 25% blue (*Poa pratensis*), 25% timothy (*Phleum pratense*), 10% red fescue (*Festuca rubra*), and 10% meadow fescue (*Festuca elatior*). Each of the pollens was defatted by successive extractions with diethylether or petroleum ether (ca. 8×1 liter amounts) and extracted at 4° C. either once with ten times the volume (ml) of 0.125 M $NH_4HCO_3$ over the weight (gm) of pollen for ca. 18 hours (with agitation), or in three serial extractions with a volume of $NH_4HCO_3$ solution totaling ten times the quantity of pollen. After centrifugation, each supernatant extract was dialyzed extensively at 4° C. in Visking size 18 cellulose casing against 0.002 M $NH_4HCO_3$ (4–5×72 liters) and finally against distilled water (1×72 liters), over a period totaling about four days. This dialysis process served to remove essentially all of the low molecular weight non-allergenic components. Each dialyzed extract was centrifuged to remove a trace amount of precipitate, lyophilized and stored at −20° C. in an air-tight container until used.

Dialyzed allergen extract (1) or (2) at 2 mg/ml was incubated with 0.5 M formaldehyde solution for 14 to 18 days at 10° C.±1° C. in 0.1 M $Na_2HPO_4/NaH_2PO_4$ buffer at pH 7.5±0.1 (Buffer A), transferred directly to an incubator at 32° C.±1° C., and incubated for a further period of 14 to 18 days. Excess formaldehyde was removed by dialysis against Buffer A, physiological buffered saline or distilled water (see discussion below).

EXAMPLE II

Dialyzed allergen extract (1) (2 mg/ml) was incubated with 0.5 M formaldehyde solution for 30 to 35 days at 10° C.±1° C. and pH 7.5±0.1 in Buffer A, transferred directly to an incubator at 32° C.±1° C., and incubated for a further period of 30 to 35 days. Excess formaldehyde was removed by dialysis against Buffer A, physiological buffered saline or distilled water.

EXAMPLE III

Dialyzed allergen extract (2) (2 mg/ml) was incubated with 0.5 M formaldehyde solution for about 8 days at 10° C.±1° C. and pH 7.5 in Buffer A, transferred directly to an incubator at 32° C.±1° C., and incubated for a further period of about 32 days. Excess formaldehyde was removed by dialysis against Buffer A, physiological buffered saline or distilled water.

EXAMPLE IV

Dialyzed allergen extract (1) or (2) (10 mg/ml) was incubated with 2 M formaldehyde solution for about 14–18 days at 10°±1° C. The solution was diluted fourfold (i.e., to 2.5 mg/ml ragweed and 0.5 M formaldehyde). The solution was reincubated for about 14–18 days at 32°±1° C. Excess formaldehyde was removed by dialysis against Buffer A, physiological buffered saline or distilled water.

EXAMPLE V

Dialyzed allergen extract (1) or (2) (8 mg/ml) was incubated with 2 M formaldehyde solution for about 14–18 days at 10°±1° C. The solution was diluted fourfold (i.e., to 2.0 mg/ml ragweed and 0.5 M formaldehyde). The solution was reincubated for about 14–18 days at 32°±1° C. Excess formaldehyde was removed by dialysis against Buffer A, physiological buffered saline or distilled water.

EXAMPLE VI

A dialyzed allergen extract (1) of short ragweed pollen (2 mg/ml) was incubated with 2 M formaldehyde solution for about 14 to 18 days at 10° C.±1° C. at pH 7.5±0.1 in 0.1 M sodium phosphate buffer (Buffer A); the solution was dialyzed extensively at 4° C. against several changes in Buffer A to remove formaldehyde; additional formaldehyde (12.3 M) was slowly added to make solution 0.36 M with respect to formaldehyde; and the solution was reincubated for 16 days at 32° C.±1° C. and pH 7.5±0.1. Excess formaldehyde was removed by dialysis against Buffer A or physiological buffered saline.

EXAMPLE VII

Dialyzed allergen extract (1) or (2) (2 mg/ml) was incubated with a mixture of 0.025 M glutaraldehyde and 0.5 M formaldehyde in Buffer A for about 18 hours at 10°±1° C. The mixture was then immediately placed at 32° C.±1° C. and incubated for about 21 days at pH 7.5±0.2. The excess glutaraldehyde and formaldehyde were removed at the end of the experiment by dialysis.

EXAMPLE VIII

Dialyzed allergen extract (1) and (2) (2 mg/ml) was incubated with 0.025 M glutaraldehyde in Buffer A for about 18 hours at 10°±1° C. Excess glutaraldehyde was removed by dialysis against Buffer A. Formaldehyde solution was added to the glutaraldehyde-treated allergen solution to make it 0.5 M with respect to formaldehyde. This mixture was then incubated for about 21 days at 32°±1° C. The excess formaldehyde was removed by dialysis at the end of the experiment.

EXAMPLE IX

Dialyzed allergen extracts (1) or (2) (2 mg/ml) was incubated with glutaraldehyde (0.025 M) at 10° C.±1° C. for about 20 hours and 30° C.±1° C. for about 24 hours at pH 7.5±0.1 in Buffer A. The excess glutaraldehyde was removed by dialysis against Buffer A or physiological buffered saline at the end of the experiment. Other glutaraldehyde concentrations were investigated (range 0.0005 to 0.1 M), but the 0.025 M was found to give the best product in terms of low allergenic activity and retention of desired immunizing properties.

EXAMPLE X

Dried short ragweed (*Ambrosia elatior*) pollen was defatted by Soxhlet extraction using petroleum ether. The refluxing action was continued until the eluant became free of the color imparted by the pollen. The pollen was air-dried, weighed and stored in tightly sealed containers at −5° to −30° C. Five milliliters of 0.125 M ammonium bicarbonate buffer per gram of defatted pollen was added to the pollen, and the mixture was extracted with constant agitation at 0° to 5° C. for 18 to 26 hours. After this first extraction, the extract was removed from the pollen grains by filtration and the pollen cake was re-extracted with 4 ml buffer/gm pollen (starting weight) for 2 to 4 hours at 0° to 5° C., followed by a rinse of 1 ml buffer/gm pollen. All three extracts were combined and dialyzed in Visking size 18 seamless cellulose tubing against a 35-fold larger volume of 0.002 M ammonium bicarbonate for 30 to 40 hours. An additional 12 to 14 hours of dialysis was carried out against distilled water. The extract was filtered through a series of filters, ending up with sterile filtration through a 0.45 m$\mu$ filter. The sterile extract was lyophilized and weighed. Incubation of this dialyzed extract (10 mg pollen solids/ml) was performed using 2 M formaldehyde in 0.1 M sodium phosphate buffer at pH 7.2 to 7.6 for 12 to 18 days at 10°±2° C.

The resultant solution was diluted 4-fold in the 0.1 phosphate buffer and incubated at pH 7.2 to 7.6 for 18 to 24 days at 32°±2° C. The resultant solution was dialyzed in Visking casing size 1⅝ in. dia. against two 35-fold volumes of 0.002 M NH$_4$HCO$_3$. The solution was checked for absence of formaldehyde, concentrated using a Millipore Pellicon Cassette System, sterile-filtered and lyophilized.

In each of the foregoing examples, incubations and dialyses were performed using 0.1 M sodium phosphate buffer, pH 7.5±0.1 and all solutions were extensively dialyzed at about 4° C. against several changes of large volumes of dialysate to remove the unreacted aldehyde at the end of each experiment. Solutions were either stored frozen, or, in several instances, the aldehyde-modified allergens were lyophilized from aqueous solutions, a process which led to essentially aldehyde-free solids having excellent long-term storage characteristics.

EXAMPLE XI

Allergen

Pollen of short ragweed (*Ambrosia elatior*) was purchased from Greer Laboratories and was stored at −20° C. in an air-tight container until used. The pollen (150 gm.) was defatted by eight successive extractions with one liter portions of anhydrous, peroxide-free diethyl ether (J. T. Baker Co.), which allowed removal of all the colored fatty material. The pollen was allowed to dry and traces of ether were evaporated in vacuo overnight. The defatted pollen was then extracted at 4° C. with gentle agitation for 18 hours with 1.5 liters of 0.125 M NH$_4$HCO$_3$, and the pollen was separated from the supernatant by centrifugation. The supernatant extract (1185 ml) was subjected to extensive dialysis in Visking size 18 cellulose casing (Union Carbide Corp.) against 0.002 M NH$_4$HCO$_3$ (5×72 liters) and finally against distilled water (2×72 liters) over a total period of four days at 4° C. The dialyzed extract was centrifuged to remove a small amount of precipitate and lyophilized (yield=14.104 gm). This material, which will be referred to as "Ragweed Pollen Allergen, Lot 11RWC", was stored at −20° C. in an air-tight container until used.

Allergoid

A portion of the lyophilized allergen was subjected to formaldehyde modification by the "two-step procedure". Ragweed pollen allergen (13.603 gm) was dissolved in 0.1 M phosphate buffer, pH 7.50[1] (453.4 ml) to give a solution containing 30 mg pollen solids per ml. This solution was dialyzed (in size 18 Visking tubing) against the phosphate buffer (11.2 liters) for 24 hours at 4° C. After dialysis, the final volume of the allergen solution was adjusted to 907 ml (15 mg pollen solids/ml with 0.1 M phosphate buffer at pH 7.50.

[1] Prepared by mixing together appropriate volumes of 0.1 M NaH$_2$PO$_4$ and 0.1 M Na$_2$HPO$_4$ (both Baker Reagent grade) to give a final pH of 7.50.

The following reaction mixture was prepared at 4° C. Ten molar formaldehyde solution (270 ml)[2] was added very slowly and carefully with constant stirring to 900 ml of the allergen solution, avoiding localized high concentrations of formaldehyde. The pH of the solution was monitored throughout, and a total of 6.5 ml 2 M NaOH (Baker Co.) was added during the mixing to keep the pH at 7.50±0.1. The final volume of the reaction mixture was adjusted to 1350 ml using 170 ml 0.2 M phosphate buffer at pH 7.50, 1.1 ml 2 M NaOH and 2.5 ml 0.1 M phosphate buffer at pH 7.50, to give a solution having the following composition: pollen solids, 10 mg/ml; formaldehyde, 2.0 M; phosphate, approximately 0.1 M, at a pH of 7.50 measured at 10° C.

[2] Prepared by dilution of reagent grade formaldehyde (Fisher Scientific Co., 37% w/w) with deionized water.

The above solution was incubated for 16 days at 10° C.±0.5° C., at which time the pH had fallen to pH 7.41. Following this first incubation, the solution was diluted 4-fold with 0.1 M phosphate at pH 7.50 and incubated at 32° C.±0.5° C. for a further 16 days. The starting pH for this second incubation was pH 7.49 (measured at 32° C.) and finishing pH was 7.47 (at 32° C.). The resultant allergoid solution was dialyzed successively against 4×72 liters of deionized water at 4° C. to remove formaldehyde and buffer salts. A trace precipitate was removed by centrifugation and the resultant solution was lyophilized, which served not only to prepare a stable dry material but also to remove possible residual minute traces of formaldehyde. The yield of "Ragweed Pollen Allergoid, 11RWF" was 13.135 gm (97.3% theoretical). The allergoid was stored at 20° C. in an air-tight container until used.

Preparation of solutions for immunotherapy

Solutions were prepared in terms of "Allergen Units/ml" or "Allergoid Units/ml" where the allergoid unit was fifty times greater than the allergen unit in terms of pollen solids and "antigen E equivalents/ml (AgE equiv./ml)".[3] Based on previous experience the stock solution of allergen 11RWC (1,000 Units/ml) was prepared to contain 10 μg AgE equiv./ml (0.28 mg non-dialyzable pollen solids/ml). In a similar way, the stock solution of allergoid 11RWF (1,000 Units/ml) was prepared at 500 μg AgE equiv./ml (14.1 mg allergoid solids/ml). The stock solutions of allergen and allergoid were sterile-filtered through a Nalgene Filter Unit, equipped with a membrane pore size 0.45 μm (Nalge Sybron Corp., Rochester, N.Y.) and each solution was subsequently dispensed into sterile vials in approximately 10 ml amounts. A total of 30 vials of allergen and 23 vials of allergoid were so prepared. Both sets of vials were numbered in the order in which they were dispensed. The vials were prepared approximately three weeks before therapy commenced and were kept at 4° C. throughout the study.

[3] In the case of the allergen, this refers to the content of antigen E; in the case of the allergoid, it refers to the content of antigen E in the allergen from which it was derived (antigen E is not directly measurable in the allergoid).

The sterilities of the allergen and allergoid solutions were examined by incubation of 0.5 ml aliquots taken from selected vials with Thioglycollate Medium, in accordance with FDA Rules and Regulations, "Paragraph 610.12, Sterility". Incubations were conducted at temperatures of 25° C. and 32° C. for periods of two weeks. In the case of the allergen solution, aliquots were taken from vials numbers 1, 11, 20 and 30. In the case of the allergoid solution, aliquots were taken from vials numbers 1, 11 and 23. All sterility test solutions were examined visually for evidence of growth on the 4th, 7th and 14th days of the incubation period. No evidence of any bacterial contamination was found by such visual examinations. At the end of the 14th day of incubation, each of the test cultures was put on to plates of trypticase soy agar with 5% sheep blood (Baltimore Biological Labs, Cockeysville, MD.) and incubated at 37° C. for 24 hours. All were found to be negative for any type of growth. All aliquots of allergen and allergoid, other than those being tested for sterility, were stored at 4° C. until used.

General toxicity tests on both the allergen and allergoid solutions were performed using the method of assay described in "Paragraph 610.11, Safety" of the FDA Rules and Regulations. These tests were performed in mice and guinea pigs under the direction of Irving Lavenstein, Ph.D., Leberco Laboratories, 123 Hawthorne Street, Roselle Park, N.J. Each mouse received 0.5 ml, and each guinea pig 5 ml, of either the allergen or allergoid stock solution administered intraperitoneally. The results of these tests show no evidence of toxicity in the case of either the allergen or allergoid, as evidenced from no unusual weight loss seven days following injection of the materials.

Immunochemical analyses

Analyses of the contents of ragweed allergens, antigen E, Ra3 and Ra5 in Ragweed Pollen Allergen, Lot 11RWC, were performed by radial immunodiffusion (Baer), H., Maloney, C. J., Norman, P. S. and Marsh, D. G., 1974, *J. Allergy Clin. Immunol.* 54:157–164) using appropriate specific antisera and reference antigens. The antigen E reference was NIH material further purified by Sephadex G75 chromatography and the Ra3 references were from Dr. Lawrence Goodfriend, McGill University, Montreal. An additional antigen E reference was obtained from Dr. T. P. King, Rockefeller University, New York. Antisera were prepared in our laboratory by immunizing rabbits or goats with the respective antigens.

Crossed immunoelectrophoresis of the allergen was also performed against rabbit anti-allergen serum using a technique analogous to that described by Weeke and Lowenstein (1973) In: *A Manual of Quantitative Immunoelectrophoresis* (eds. N. H. Axelsen, J. Kroll and B. Weeke) Universitetsforlaget, Oslo, pp. 149–153.

Standard "protein nitrogen unit (PNU)" determinations of the allergen and allergoid were made according to routine FDA-approved procedures by Mr. Bill White, Jr. and associates of Greer Laboratores, Lenoir, N.C.

Patients

Fourteen ragweed-allergic Caucasian paid volunteers (7 male, 7 female; mean age 33; age rang 25 to 44) were selected for the study according to the following criteria. All patients reported severe hay fever during the ragweed season, with grass hay fever being exhibited moderately in three subjects and mildly in a further three individuals. Patients with any report of asthma were specifically excluded from the study. Also, patients with severe symptoms during July were excluded. Since earlier studies had revealed that immunotherapy with ragweed extracts influences subsequent immunologic response, any prior treatment with ragweed extract automatically excluded patients from the study. Finally, all patients were judged as good study candidates in terms of employment and emotional stability.

The patients were matched into seven pairs according to their pre-treatment leukocyte histamine-release and skin-test sensitivities to allergen and allergoid, and total serum IgE levels.

Treatment regimen

Patients were scheduled for treatment between late May and mid-August, 1977. On the first treatment day (day 0), they received courses of one-to-five injections of increasing amounts of allergen or allergoid over periods of thirty minutes to two hours until local wheal and erythema reactions or systemic symptoms indicated that the dosage was near or at the tolerated level. A complete record of injections and immediate local and systemic reactions for each patient was taken by the attending physician. Delayed local reactions at the injection sites and systemic symptoms (if any) were recorded by the patient. Medical consultation was available to all patients during the 24-hour period following the injection series, and the information on each form was confirmed by telephone interview with each patient. All local reactions were graded according to their maximum intensity which usually occurred about 24 hours following injection. (Information concerning the grading of local and systemic reactions is given in the footnote of Table V).

After the first course, serum IgG antibody to antigen E was measured at intervals of approximately 4 to 14 days, and second and subsequent courses were given as antibody responses attained successive plateau levels in the patients. Reactions to the injections were recorded at each occasion as described above. Six allergen- and six allergoid-treated patients complied with our study regimen, each receiving four or five injection courses between late May and mid-August, 1977 (Tables I and II).

TABLE I

Dosages and Numbers of Injections per Course for Allergen-Treated Patients

| Pair No. | Patient | 1st | 2nd | 3rd | 4th | 5th | Cumulative Totals |
|---|---|---|---|---|---|---|---|
|   |   | Allergen Units (No. of injections in parens) |  |  |  |  |   |
| 1. | E.E. | 6(4)+ | 15(2) | 10(1) | 60(2) | 50(1) | 141(10) |
| 2. | L.L. | 31(4) | 170(3) | 50(1) | 350(3) | 1200(3) | 1801(14) |
| 3. | M.K. | 31(4) | 70(2)* | 50(2) | 50(1)* | 30(1) | 231(10) |
| 4. | G.J. | 6(3) | 15(2) | 10(1) | 60(2)* | 20(1) | 111(9) |
| 5. | B.D. | 4(5) | 17(3) | 70(2) | 150(2)* | 100(2) | 341(14) |
| 7. | L.D. | 36(4) | 164(3) | 200(1) | 700(2) | 500(1) | 1601(11) |
|   | Means | 19(4.0) | 75(2.5) | 65(1.3)† | 228(2.0) | 317(1.5) | 704(11.3)‡ |
| Dropout: |  |  |  |  |  |  |  |
| 6 | S.B. | 31(4) | 170(3)* | 25(1) | — | — | 226(8) |

*Systemic reaction.
†Two injections per day were administered on two successive days.
‡The mean cumulative dosage for all patients, excluding S.B., is equal to 7.04μg AgE equivalents.

TABLE II

Dosages and Numbers of Injections per Course for Allergoid-Treated Patients

| Pair No. | Patient | 1st | 2nd | 3rd | 4th | 5th | Cumulative Totals |
|---|---|---|---|---|---|---|---|
| | | \multicolumn{5}{c}{Allergoid Units (No. of injections in parens)} | | |
| 1. | E.F. | 31(4) | 170(3) | 100(1) | 200(2) | 200(2) | 701(12) |
| 2. | D.H. | 16(4)* | 2(1) | 5(2) | 16(3) | — ¶ | 40(10) |
| 3. | G.D. | 32(4) | 70(2) | 125(2) | 310(2) | 1200(3) | 1737(13) |
| 4. | J.B. | 31(4) | 170(3) | 70(2) | 300(2) | 1200(3) | 1771(14) |
| 5. | J.K. | 37(4) | 70(2) | 150(2) | 300(2) | 300(2) | 857(12) |
| 7. | M.B. | 32(3) | 170(3) | 300(2) | 1200(3) | — | 1702(11) |
| | Means: | 30(3.8) | 109(2.3) | 125(1.8) | 388(2.3) | 725(2.5) | 1135(12)‡ |
| Dropout: | | | | | | | |
| 6 | P.J. | 26(4) | 5(1) | 6(2) | 5(1) | — ¶ | 42(8) |

*Systemic reaction.
¶Fifth injection course was not given
†The mean cumulative dosage for all patients, excluding P.J., is equal to 567.35µg AgE equivalents.

Assays of relative allergenicity, allergoid/allergen

The relative allergenicities of allergoid to allergen in our study subjects were determined both by leukocyte histamine release assay (Marsh, D. G., Lichtenstein, L. M. and Campbell, D. H., 1970, Immunology, 18: 705-722), and quantitative intradermal endpoint skin titration (Norman, P. S., 1976, In: Manual of Clinical Immunology (eds. N. R. Rose and H. Friedman), American Soc. for Microbiol., Washington, D.C., p. 585). Each patient's leukocyte sensitivity ratio was expressed as the ratio of allergoid/allergen concentrations producing 50% histamine release from the patient's leukocytes. His skin-test sensitivity ratio was the ratio of the allergoid/allergen concentrations producing two-plus (8 to 10 mm wheal diameter with erythema) skin-test endpoints.

Total serum IgE assays

Measurement of total serum IgE in one pre- and three post-treatment sera from all patients was performed by a "direct RIST" procedure developed by Shellenberg and Adkinson (Schellenberg, R. R. and Adkinson, N. F. 1975. J. Immunol. 115:1577–1583). The method was similar to the "PRIST" method of Wide (Wide, L. 1971. In: Radioimmunoassay Methods (eds. K. E. Kirkham and W. M. Hunter), Livingstone, Edinburgh, p. 173), except that the first stage of the assay utilized specific anti-IgE antibody (raised in a goat) coupled to Sepharose 4B rather than to paper discs. Following incubation of the patient's serum with the Sepharose immunoadsorbent beads, the beads were washed and subsequently incubated with radiolabeled rabbit anti-IgE ($\epsilon$-chain specific purified antibody). The beads were then washed again and counted in a gamma counter. The counts were compared with those obtained with serial titrations using a control serum of known IgE content. The above experiments were all run in duplicate with appropriate positive and negative controls and three internal standard sera of known IgE content. Also, each assay was repeated at least once, and any discrepant values (differing from one another by more than ±10%) were repeated until values with ±10% were obtained.

Assay of serum IgG antibody to antigen

Immunoglobulin G antibody to antigen E was measured using a highly sensitive double antibody radioimmunoassay procedure similar to that described by Black et al (Black, P. L., Marsh, D. G., Jarrett, E., Delespesse, G. J. and Bias, W. B. 1976. Immunogenetics 3:349–368). Purified antigen E was labeled with $^{125}I$ by the Chloramine T procedure, ultracentrifuged to remove microaggregates and stored at −70° C. in small aliquots until used. Appropriate serial 2-fold dilutions of a standard serum (from an allergic subject who had been extensively treated with ragweed extract), the sera from study patients and appropriate controls were incubated with the constant amount of the labeled antigen E (approximately 1.2 ng at concentration 6.2 ng/ml) for five hours at 23° C.[4] All serum samples were diluted 1:50 in borate-buffered saline (BBS), pH 8.0, and appropriate further dilutions were made in BBS containing 1:50 normal human serum devoid of antibody to antigen E. Negative control tubes consisted of a 1:50 dilution of this normal serum. Following the initial incubation, serum IgG (and bound antigen-antibody complexes) was precipitated by addition of a slight excess of goat anti-IgG (anti-Fc fragment) and overnight incubation at 4° C. The resultant precipitates were washed and counted, and the test sera compared with the standard control curve. All results were expressed in arbitrary "Units of IgG antibody/ml serum" based on the control serum curve. In previous studies (Platts-Mills, T. A. E., vonMaur, R. K., Ishizaka, K., Norman, P. S. and Lichtenstein, L. M. 1976 J. Clin. Invest. 57:1041–1050) it has been shown that the undiluted control serum will bind about 24 µg antigen E/ml in antigen excess. On this basis, we calculated that one of our arbitrary units would be expected to bind 1.3 ng antigen E in antigen excess. Assuming that, under such conditions, the bound antigen exists as $Ag_2Ab$ complexes, one Unit$\simeq$12.8 ng antibody. Under the limiting antigen concentrations of our assay, less antigen will bind and the effective antibody concentration may be about 3-fold less. (Platts-Mills, T. A. E., Snajdr, M. J., Ishizaka, K. and Frankland, A. W., 1978, J. Immunol., 120:1201–1210).

[4]In order to increase the sensitivity of the assay for low concentrations of antibody, the nonspecific binding of radioactivity (primarily to the plastic assay tubes) was reduced both by precoating the assay tubes with bovine serum albumin, 0.3% (w/v) and by diluting the labeled antigen in 5% (w/v) albumin.

Fourteen to sixteen serum samples from each of the patients completing the study, and several samples from each of the two drop-outs were analyzed. In order that changes in IgG antibody titers could be rapidly evaluated to allow appropriate timing of the injection sequence, we measured these antibody responses within about three days after drawing the blood specimens. All assays were run in duplicate in each experiment and were repeated on the succeeding experiment. Assays were repeated as necessary until values within ±10% were obtained.

Blood chemistries and urinalysis

Blood chemistry measurements and urinalyses were performed before immunotherapy and about one and about fourteen weeks after completion of therapy. Standard SMA-11 blood chemistries were determined by The Good Samaritan Hospital Clinical Laboratory utilizing automated analytical procedures. Standard urinalyses were performed in our allergy laboratory.

Symptom evaluation

Hay-fever symptoms during the ragweed pollination season were evaluated by each patient twice a day on a standard record. Average daily symptom scores (Normam, P. S. and Winkenwerder, W. L., 1965, *J. Allergy*, 36:284–292) for groups of hay-fever patients have been found to correlate with daily pollen counts. In addition to these self-evaluations, each patient was interviewed by an attending physician twice during the ragweed season.

Results

Table III presents the immunochemical analyses of the allergen and allergoid.

dialyzable peptide material). Ragweed antigen E, Ra3 and Ra5 are not measurable in the allergoid; hence we refer to concentrations in terms of "AgE equiv./ml", etc., based on the respective antigen contents of the native ragweed allergen.

Table IV shows the histamine-release, skin-test and total IgE data for the seven pairs of patients at the beginning of the study.

TABLE IV

Pre-treatment sensitivities to Allergen and Allergoid and Total IgE Data

| Pair No. | | Sens. to Allergen* (ALLERGEN-TREATED) | Sens. to Allergoid* | Ratios Goid/Gen | Total IgE U/ml | | Sens. to Allergen (ALLERGOID-TREATED) | Sens. to Allergoid | Ratios Goid/Gen | Total IgE U/ml |
|---|---|---|---|---|---|---|---|---|---|---|
| 1 | HR | $6.0 \times 10^{-4}$ | $4.0 \times 10^{-2}$ | 67 | 218 | HR | Not determined | — | | 196 |
|   | ST | $10^{-5}$ | $3 \times 10^{-3}$ | 300 | | ST | $10^{-5}$ | $3 \times 10^{-3}$ | 300 | |
| 2 | HR | $6.8 \times 10^{-5}$ | $6.0 \times 10^{-3}$ | 88 | 88 | HR | $4.0 \times 10^{-5}$ | $9.0 \times 10^{-4}$ | 23 | 710 |
|   | ST | $10^{-4}$ | $10^{-2}$ | 100 | | ST | $10^{-6}$ | $3 \times 10^{-4}$ | 300 | |
| 3 | HR | V. low release | — | | 174 | HR | 24%† | 23%† | ~100 | 113 |
|   | ST | $10^{-5}$ | $10^{-2}$ | 1000 | | ST | $10^{-4}$ | $10^{-1}$ | 1000 | |
| 4 | HR | $5.4 \times 10^{-5}$ | $2.2 \times 10^{-1}$ | 278 | 119 | HR | $1.0 \times 10^{-3}$ | $1.8 \times 10^{-1}$ | 180 | 85 |
|   | ST | $10^{-5}$ | $10^{-2}$ | 1000 | | ST | $3 \times 10^{-5}$ | $10^{-2}$ | 300 | |
| 5 | HR | $2.3 \times 10^{-4}$ | $2.2 \times 10^{-1}$ | 957 | 107 | HR | $1.1 \times 10^{-4}$ | $1.5 \times 10^{-2}$ | 136 | 120 |
|   | ST | $10^{-5}$ | $10^{-2}$ | 1000 | | ST | $10^{-5}$ | $10^{-3}$ | 100 | |
| 6 | HR | $1.2 \times 10^{-4}$ | $3.6 \times 10^{-2}$ | 300 | 28 | HR | $1.0 \times 10^{-4}$ | $7.0 \times 10^{-2}$ | 700 | 45 |
|   | ST | $3 \times 10^{-5}$ | $10^{-3}$ | 30 | | ST | $10^{-4}$ | $10^{-1}$ | 1000 | |
| 7 | HR | No release | — | | 679 | HR | 37% | No. rel. | — | 15 |
|   | ST | $10^{-3}$ | $\sim 3 \times 10^{0}$ | ~3000 | | ST | $10^{-5}$ | $10^{-2}$ | 1000 | |
| Geom. Means | HR‡ | $1.4 \times 10^{-4}$ | $5.3 \times 10^{-2}$ | 216 | 135 | HR‡ | $1.4 \times 10^{-4}$ | $2.0 \times 10^{-2}$ | 132 | 102 |
|   | ST | $3 \times 10^{-5}$ | $7 \times 10^{-3}$ | 432 | | ST | $2 \times 10^{-5}$ | $7 \times 10^{-3}$ | 432 | |

*Concn. (μg/ml) eliciting 50% histamine release (HR) or a two-plus skin test (ST).
†Low release; max. percent release cited. Ratios estimated where possible.
‡Excludes patients with unmeasurable values.

TABLE III

| Immunochemical Analysis of the Antigens | |
|---|---|
| Ragweed Pollen Allergen, 11RWC: | 35.5μg AgE/mg lyophilized solids. |
| | 6.5μg Ra3/mg lyophilized solids. |
| | 6.0μg Ra5/mg lyophilized solids. |
| | 6390 PNU/mg lyophilized solids. |
| Ragweed Pollen Allergoid, 11RWF: | 35.5μg AgE equiv./mg lyoph. solids. |
| | 6100 PNU/mg lyophilized solids. |
| 1 Allergen Unit = 0.01μg AgE equiv. = | 1.8 PNU ⎫ |
| | ⎬ 50-fold difference by weight |
| 1 Allergoid Unit = 0.5μg AgE equiv. = | 86 PNU ⎭ |

Analyses of other similar preparations of lyophilized dialyzed ragweed allergen showed the following mean antigenic compositions: AgE (5 preps.) = 24.3μg/mg (range: 11.3–41.1μg/mg); Ra3 (4 preps.) = 7.1μg/mg (range: 5.0–9.4μg/mg); Ra5 (4 preps.) = 4.1μg/mg (range 2.3–6.1μg/mg).

The contents of antigen E, Ra3 and Ra5 in the allergen are generally higher than the average values obtained by analyzing several different batches of lyophilized allergen (see footnote to Table III). The PNU values for allergen and allergoid are similar, as expected. (It should be noted that non-dialyzed ragweed extracts containing the same amounts of non-dialyzable pollen solids give about twice these PNU values due to the fact that the technique measures some nitrogen in All patients except those in pair No. 6 complied with our study regimen, and subsequent comparisons will refer primarily to the twelve individuals who completed the study. We found it extremely difficult to match our patients completely in terms of all the criteria, but the geometric mean histamine-release and skin-test sensitivities to allergen and allergoid and total serum IgE levels were reasonably well matched.

Tables I and II summarize the injection doses, in terms of Allergen or Allergoid Units, for the allergen- and allergoid-treated groups. All six allergen-treated patients complying with our study regimen received five courses of injections, with between one and five treatments for each course. In the allergoid-treated group, two of the patients received only four courses and the remainder received five courses. The mean cumulative dose for allergoid-treated patients was 567 μg AgE equiv. (1135.7 Units) which is 80.6 times greater than the mean cumulative dosage of 7.0 μg AgE equiv. (704 Units) for the allergen-treated group. In general, dosages could be substantially increased at each new course, the main hindrance being the occurrence of five systemic reactions in the allergen-treated group (including one in the patient who dropped out) and one in the allergoid-treated group; these are indicated by asterisks in Tables I and II, and are rated according to the frequency and severity in Table V.

TABLE V

Scoring of Local and Systemic Reactions Following Injection of Allergen (Gen) or Allergoid (Goid)

| Pair No. | Local (24 hr.) | | Systemic | |
|---|---|---|---|---|
| | Gen | Goid | Gen | Goid |
| 1 | 9 | 17 | 0 | 0 |
| 2 | 20 | 19 | 0 | 2 |
| 3 | 16 | 15 | 2 | 0 |
| 4 | 17 | 4 | 2 | 0 |
| 5 | 3 | 14 | 1 | 0 |
| 7 | 1 | 4 | 0 | 0 |
| Total scores: | 66 | 73 | 5 | 2 |
| Average per patient: | 11.0 | 12.2 | 0.86 | 0.33 |
| Average per injection: | 2.2 | 2.6 | 0.17 | 0.07 |
| Dropouts: | | | | |
| 6 | 0 | 8 | 1 | 0 |

Local reactions were graded as follows:
1+ (1 point): any swelling up to 10 cm in diameter;
2+ (2 points): 10-20 cm diameter swelling;
3+ (3 points): larger than 20 cm but reaching no further than elbow;
4+ (4 points): swelling reaching below elbow (did not occur in this series).
Systemic reactions were graded as follows:
1+ (1 point): any systemic symptoms beyond local area of injection, but not requiring epinephrine;
2+ (2 points): hives, hay-fever or asthma symptoms requiring epinephrine, blood pressure remains normal;
3+ (3 points): systemic allergic symptoms with lowering of blood pressure (did not occur in this series);
4+ (4 points): frank anaphylaxis requiring emergency measures (did not occur).

The systemic reactions occurred within half an hour following antigen administration and, if necessary, were promptly reversed by administration of epinephrine. The principal other adverse reactions consisted of localized swelling at the sites of administration of the higher antigen doages. These reactions started at approximately six hours and reached their maximal at approximately 24 hours following the injections. The average scores for such localized reactions was about the same in both patient groups (Table V).

Examination of the blood-chemistry (SMA-11) and urinanalytical data reveals no adverse toxic responses occurred as a result of treatment with either allergoid or allergen.

Since it was necessary to perform repeated double antibody radioimmunoassay experiments for the measurement of serum IgG antibody to antigen E, considerable care was taken to ensure good reproducibility from one experiment to another. FIG. 1 illustrates the high degree of reproducibility obtained for the standard curves in fourteen of fifteen of the assays performed. The standard curve for the remaining assay was outside the limits of the other assays and the data for this experiment were discarded. Since antibody measurements were performed for single serum dilutions throughout most of the study, it was essential to ensure that the slopes of the binding curves for each patient were indistinguishable from that of the control. Therefore, we took a randomly chosen serum from each patient and assayed the full binding curves, we found that the binding curves for each patient were not significantly different from those of the standard (FIG. 2), providing the essential rationale for our utilization of a single dilution in assaying antibody levels in the remaining sera.

Figure 3:
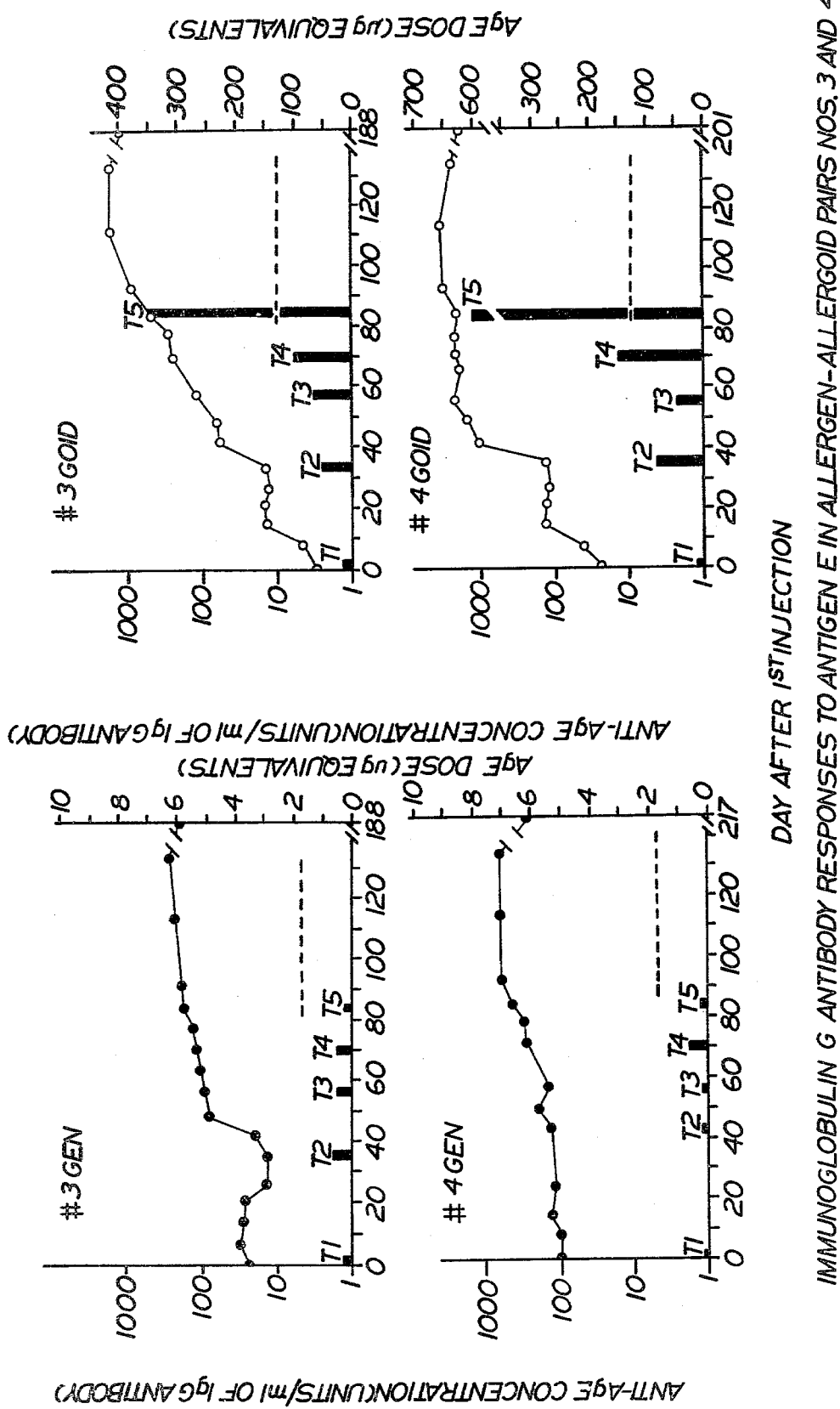
Figure 4:
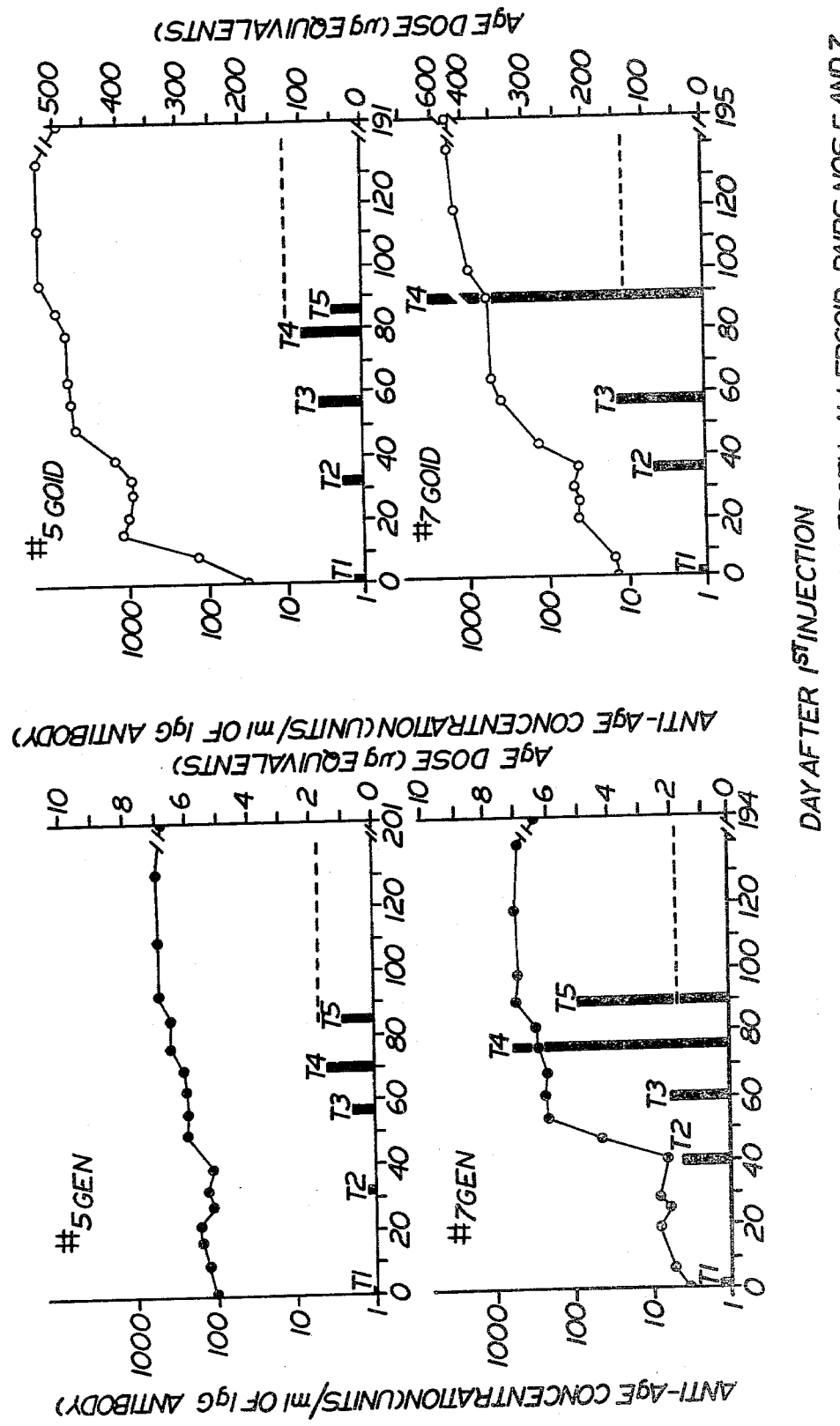
Figure 5:
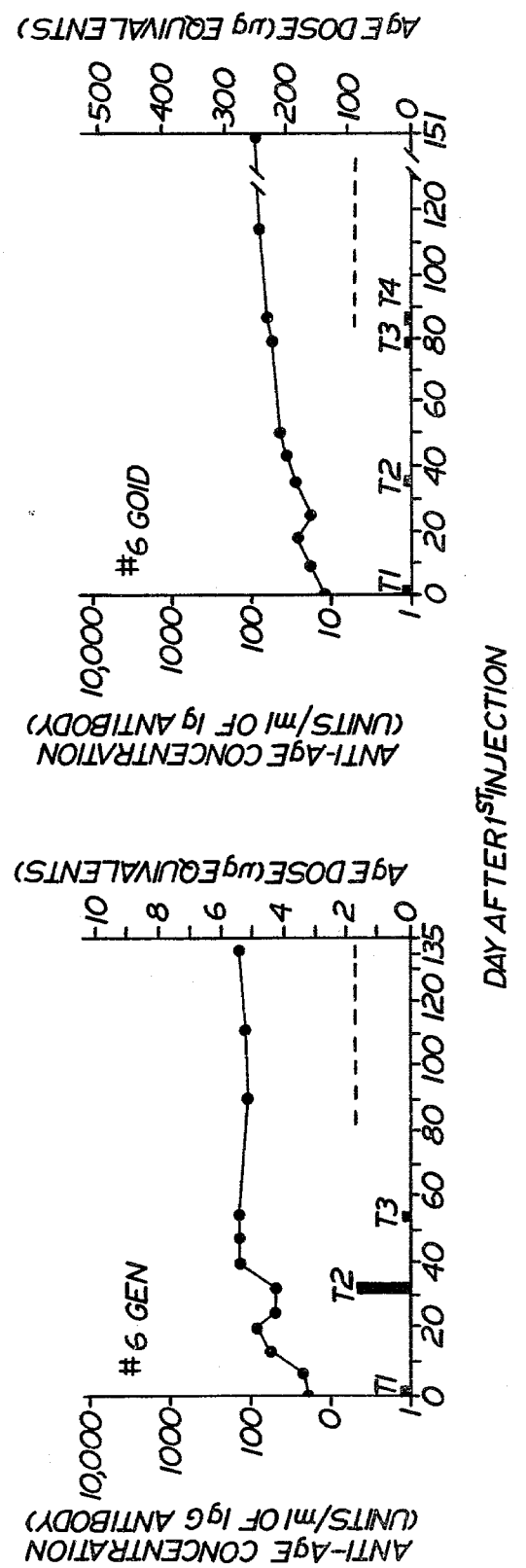
Figure 6:
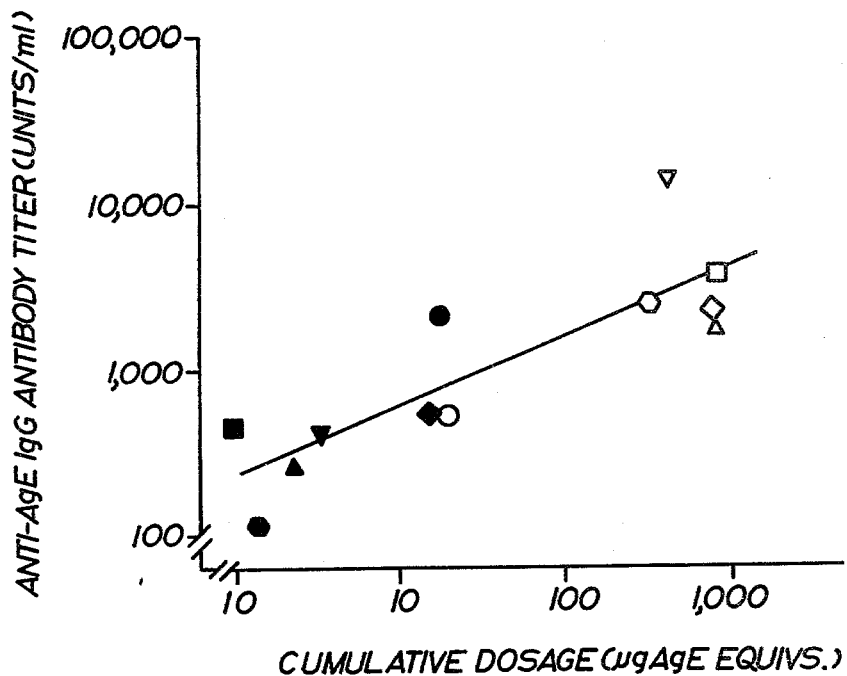

FIGS. 2-4 show the anti-antigen E IgG responses in the six pairs of patients who complied our study regimen and FIG. 6 shows the two drop-outs. Following the first series of injections at day 0, the IgG antibody titers rose significantly in most patients and reached plateau levels at between two and three weeks. Having established that plateau levels have indeed been achieved in most patients by measuring antibody titers in a series of four-to-five successive blood samples, we gave a second series of injections between days 28 and 42. After about a further three to four weeks, we appeared to be reaching secondary plateau levels in most patients and gave a further course of injections. A further two or three injection courses were administered before the ragweed season in mid-August. Due to shortage of time before the season, we were unable to wait to ensure that plateau levels had been obtained in all patients between the administration of these latter courses.

FIGS. 2-5 illustrate that the patients started with widely differing antibody levels prior to treatment (3-114 Units/ml). Antibody levels rose in all patients following treatment, with the allergoid-treated group having a 5.7-fold higher geometric mean rise and a 5.2-fold higher peak titer than the allergen-treated group. With the exception of pair No. 2, all allergoid-treated patients produced larger antibody rises—usually 5-fold to 20-fold larger—their allergen-treated counterparts. Of further importance is the finding that, following only two courses of immunization, allergoid-treated patients produced, on average, 47% (range 15% to 91%) of the maximum antibody responses attained following the full four-to-five course treatment. The corresponding data for allergen-treated individuals was 32% (range 6% to 43%) of maximum response after two injection courses. The geometric mean rise after only two courses of treatment was 7.9-fold greater in the allergoid- than the allergen-treated group. Unexpectedly, we found that all except one patient (G.T., Gen. No. 4) retained IgG antibody titers to within 50% to 100% of their peak levels some 3½ months following the last injection, which is two months after the ragweed season.

FIG. 6 illustrates the relationship between cumulative antigen dosage (expressed in μg AgE equiv.) and the overall increases in IgG antibody responses (peak response minus initial level) for all twelve patients who completed the study. There was a clear relationship between antibody response and dosage independent of whether a patient was treated with allergen or allergoid. Since the regression lines for the two groups were not significantly different, we have pooled data for all twelve patients. By linear regression analysis of log (antibody titer) versus log dosage, the correlation coefficient, $r = 0.83$; $p < 0.001$. The corresponding data for antibody response versus cumulative dosage after only two injection courses showed a similar correlation ($r = 0.81$; $p < 0.001$).

Figure 8:
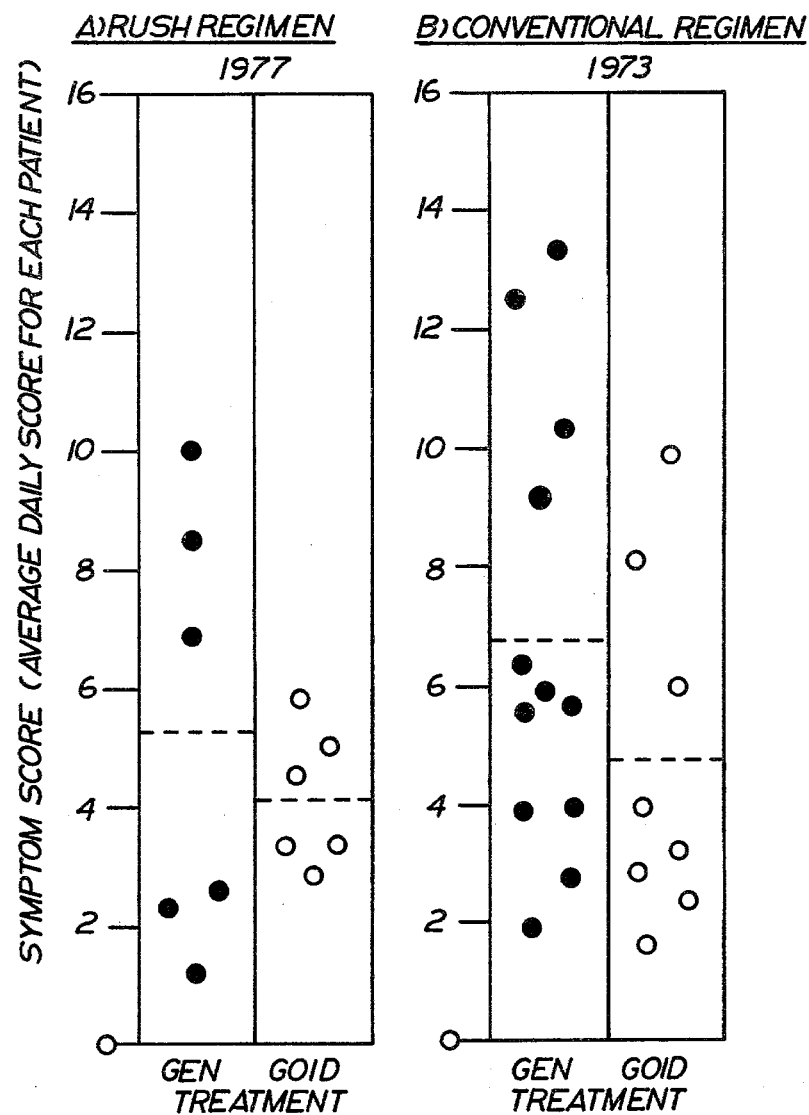

The mean day-to-day symptom scores in the two groups of patients over the 1977 ragweed pollen season (FIG. 7) show a trend toward lower overall symptomatology throughout the season. This is borne out by analysis of the mean daily scores for each patient, averaged over the entire ragweed season (FIG. 8A). The mean score for the allergoid-treated group was 1.1 symptom units less than the allergen-treated group. These results were not statistically different with these few patients. Previous studies (Norman, P. S., Winkenwerder, W. L. and Lichtenstein, L. M. 1971. *J. Allergy* 47:273) have shown that the mean daily symptom scores for the whole ragweed season for similarly sensitive placebo-treated patients normally fall in the range of seven to ten units, weak peak mean daily scores of twelve to fourteen units. Therefore, most of the treated patients seem to be doing better than would have been expected for a matched placebo group. The scores of our treated patients are similar to those found in patients (also previously untreated) who underwent a conventional treatment regimen of sixteen to twenty-four weekly injections of antigen in our 1973 study of allergen versus allergoid (FIG. 8B). The physician's evaluations of the patients during the ragweed season concurred with the above self-evaluated symptom scores.

Discussion

The present study represents the first systematic attempt to try to define the optimal treatment regimen, in terms of antigen dosage and injection spacing, for the immunotherapy of allergic patients. Toward this end, we have utilized an intensive "rush" regimen comprising of one to five injections on each treatment day. This protocol allows the clinician to administer an optimally tolerated dosage to the patient. In most cases such dosages are some 100 to 10,000 times greater than those normally administered on the first day of a patient's treatment. In the case of the allergoid, the high treatment dosage on the first injection day results in a substantial (10 to 100-fold) increase in IgG antibody to antigen E some two-to-three weeks later. A second course of injections at higher dosages can then be administered which results in an antibody response which averages about 50% of that subsequently attained following two or three further courses of injection with high doses of allergoid.

It would appear from our antibody studies that an injection spacing of two-to-four weeks may be optimal since, by this time, the patient has attained maximal responses to the immunization. However, it is possible that a somewhat greater interval allowing for additional recruitment of IgG antibody-producing cells, may prove to be somewhat more efficacious, provided antibody levels are not allowed to fall too drastically.

Despite the high dosage regimens (especially with allergoid), no adverse toxic responses were noted in any of the treated patients.

These studies show clear advantages of allergoid over allergen in that very high doses of allergoid can be administered to the patient with a relatively low risk of systemic reactions, and with resultant high levels of IgG antibody. In our study, the one exception to this rule was patient D. H. in allergoid pair No. 2. This individual showed higher than average sensitivity to allergoid and, retrospectively, it seems likely that the initial treatment course was pushed too hard in his case. The incidence of systemic reactions in the allergen-treated groups averaged 0.7 per patient, with an average reaction score of 0.8 per patient (includes the dropout). This is unacceptably high for us to recommend such an intensive dosage schedule for rush treatment with allergen.

This study, performed in two small groups of patients treated with allergen and allergoid encourages us to proceed with larger patient groups comparing the conventional treatment regimen for allergen with the modified rush regimen for allergoid.

Having fully described the invention, it is intended that it be limited only by the lawful scope of the appended claims.

I claim:

1. A process for producing an aldehyde-treated allergen of low allergenic reactivity in allergic humans and which retains the desired immunizing properties of the native allergen leading to amelioration of the symptomatology of allergic individuals and concomitant production of blocking antibody considered to be associated with, but not necessarily uniquely responsible for, such relief of symptoms, and which is capable of inducing in mammals the formation of blocking antibodies against the native allergen in significant concentration which comprises allowing allergens from which essentially all low molecular weight, non-allergenic substances have been removed to react chemically under mild conditions with an aldehyde solution selected from the group consisting of formaldehyde, lower saturated aliphatic di-functional aldehydes and combinations thereof, in at least two steps with the provisos that any formaldehyde reactions are carried out in a non-phenolic environment and wherein said mild conditions comprise a reaction step which is carried out at a temperature of from just above the freezing point of the solution to 15° C., and at least one subsequent step which is carried out at a temperature of from about 25° C. to 40° C., with any combination of formaldehyde, said dialdehyde or mixture thereof in each of the successive steps, to form a product having intra- or inter-molecular crosslinking induced by said aldehydes and the allergenic determinant groups are modified to result in substantial reduction of allergenic properties while largely retaining the desired immunizing properties.

2. The process of claim 1 wherein the aldehyde in all steps is formaldehyde.

3. The process of claim 1 wherein the aldehyde in all steps is a dialdehyde having the formula:

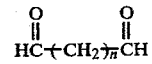

wherein n is an integer of from 1 to about 6.

4. The process of claim 1 wherein the aldehyde in all steps is glutaraldehyde.

5. The process of claim 1 wherein the aldehyde is a combination of formaldehyde and dialdehydes utilized as a mixture in each step.

6. The process of claim 1 wherein the aldehyde is a combination of formaldehyde and glutaraldehyde utilized as a mixture in each step.

7. The process of claim 1 wherein the allergens are allowed to react with said aldehyde in two steps.

8. A process of claim 1 wherein there is present along with said aldehyde solution at least one additive selected from the group consisting of 1,4-diaminobutane, lysine, ornithine, 1,5-diamino-pimelic acid, arginine, adipamide, aspartic acid, serine and alanine.

9. The process of claim 1 wherein the allergen-containing material is an aqueous extract of a pollen substance.

10. The process of claim 1 wherein the allergen-containing material is an aqueous extract of a grass pollen substance.

11. The process of claim 1 wherein the allergen-containing material contains a Group I grass pollen allergen preparation.

12. The process of claim 1 wherein the allergen-containing material is an aqueous extract of a weed pollen substance.

13. The process of claim 1 wherein the allergen-containing material is an aqueous extract of a tree pollen substance.

14. The process of claim 1 wherein the allergen-containing material contains ragweed pollen's Antigen E.

15. The process of claim 1 wherein the allergen-containing material is an aqueous extract selected from the group consisting of those containing house dust mites, house dust mite residues and mixtures thereof.

16. The process of claim 1 wherein the allergen-containing material is an aqueous extract of a member selected from the group consisting of a fungus and mixtures of fungi.

17. The process of claim 1 wherein the allergen-containing material is an aqueous extract of a member selected from the group consisting of an insect, an insect product, and mixtures thereof.

18. The process of claim 1 wherein the allergen-containing material is an aqueous extract of a member selected from the group consisting of animal dander, animal skin, animal hair and mixtures thereof.

19. The process of claim 1 wherein the allergen-containing material is an aqueous extract of food allergen.

20. The product of the process of claim 1.
21. The product of the process of claim 2.
22. The product of the process of claim 3.
23. The product of the process of claim 4.
24. The product of the process of claim 5.
25. The product of the process of claim 6.
26. The product of the process of claim 7.
27. The product of the process of claim 8.
28. The product of the process of claim 9.
29. The product of the process of claim 10.
30. The product of the process of claim 11.
31. The product of the process of claim 12.
32. The product of the process of claim 13.
33. The product of the process of claim 14.
34. The product of the process of claim 15.
35. The product of the process of claim 16.
36. The product of the process of claim 17.
37. The product of the process of claim 18.
38. The product of the process of claim 19.

39. A process for producing an aldehyde-treated allergen of low allergenic reactivity in allergic humans and which retains the desired immunizing properties of the native allergen leading to amelioration of the symptomatology of allergic individuals and concomitant production of blocking antibody considered to be associated with, but not necessarily uniquely responsible for, such relief of symptoms, and which is capable of inducing in mammals the formation of blocking antibodies against the native allergen in significant concentration, which comprises allowing allergens from which essentially all low molecular weight, non-allergenic substances have been removed to react chemically under mild conditions with a solution of formaldehyde in at least two steps, said formaldehyde reactions being carried out in a non-phenolic environment, and wherein said mild conditions comprise a reaction step which is carried out using a formaldehyde concentration of about 0.5 M to 2.5 M at a temperature of from just above the freezing point of the solution to 15° C., and at least one subsequent step which is carried out using a formaldehyde concentration of about 0.36 M to 0.5 M at a temperature of from about 25° C. to 40° C., to form a product having intra- or inter-molecular crosslinking induced by said formaldehyde and the allergenic determinant groups are modified to result in substantial reduction of allergenic properties while largely retaining the desired immunizing properties of the native allergen.

40. The product of the process of claim 39.

41. A process for producing an aldehyde-treated allergen of low allergenic reactivity in allergic humans and which retains the desired immunizing properties of the native allergen leading to amelioration of the symptomatology of allergic individuals and concomitant production of blocking antibody considered to be associated with, but not necessarily uniquely responsible for, such relief of symptoms, and which is capable of inducing in mammals the formation of blocking antibodies against the native allergen in significant concentration, which comprises allowing allergens from which essentially all low molecular weight, non-allergenic substances have been removed to react chemically under mild conditions with a solution of lower saturated aliphatic di-functional aldehydes in at least two steps, wherein said mild conditions comprise a reaction step which is carried out using a difunctional aldehyde concentration of about 0.01 M to 0.1 M at a temperature of from just above the freezing point of the solution to 15° C., and at least one subsequent step which is carried out using a difunctional aldehyde concentration of about 0.01 M to 0.1 M at a temperature of from about 25° C. to 40° C., to form a product having intra- or inter-molecular crosslinking induced by said aldehydes and the allergenic determinant groups are modified to result in substantial reduction of allergenic properties while largely retaining the desired immunizing properties of the native allergen.

42. The product of the process of claim 41.

43. A process for producing an aldehyde-treated allergen of low allergenic reactivity in allergic humans and which retains the desired immunizing properties of the native allergen leading to amelioration of the symptomatology of allergic individuals and concomitant production of blocking antibody considered to be associated with, but not necessarily uniquely responsible for, such relief of symptoms, and which is capable of inducing in mammals the formation of blocking antibodies against the native allergen in significant concentration, which comprises allowing allergens from which essentially all low molecular weight, non-allergenic substances have been removed to react chemically under mild conditions with a solution of an aldehyde in at least two steps comprising a formaldehyde reaction step which is carried out in a non-phenolic environment under mild conditions using a formaldehyde concentration of about 0.5 M to 2.5 M at a temperature of from just above the freezing point of the solution to 15° C., and at least one subsequent step which is carried out using a lower saturated aliphatic difunctional aldehyde concentration of about 0.01 M to 0.1 M at a temperature of from about 25° C. to 40° C., to form a product having intra- or inter-molecular crosslinking induced by said aldehydes and the allergenic determinant groups are modified to result in substantial reduction of allergenic properties while largely retaining the desired immunizing properties of the native allergen.

44. The product of the process of claim 43.

45. A process for producing an aldehyde-treated allergen of low allergenic reactivity in allergic humans and which retains the desired immunizing properties of the native allergen leading to amelioration of the symptomatology of allergic individuals and concomitant production of blocking antibody considered to be associated with, but not necessarily uniquely responsible for, such relief of symptoms, and which is capable of inducing in mammals the formation of blocking antibodies against the native allergen in significant concentration, which comprises allowing allergens from which essentially all low molecular weight, non-allergenic substances have been removed to react chemically under mild conditions with a solution of an aldehyde in at least two steps comprising a difunctional aldehyde reaction step which is carried out under mild conditions using a lower saturated aliphatic difunctional aldehyde concentration of about 0.01 M to 0.1 M at a temperature of from just above the freezing point of the solution to 15° C., and at least one subsequent step which is carried out in a non-phenolic environment using a formaldehyde concentration of about 0.36 M to 0.5 M at a temperature of from about 25° C. to 40° C., to form a product having intra- or inter-molecular crosslinking induced by said formaldehyde and the allergenic determinant groups are modified to result in substantial reduction of allergenic properties while largely retaining the desired immunizing properties of the native allergen.

46. The product of the process of claim 45.

47. A process for producing an aldehyde-treated allergen of low allergenic reactivity in allergic humans and which retains the desired immunizing properties of the native allergen leading to amelioration of the symptomatology of allergic individuals and concomitant production of blocking antibody considered to be associated with, but not necessarily uniquely responsible for, such relief of symptoms, and which is capable of inducing in mammals the formation of blocking antibodies against the native allergen in significant concentration, which comprises allowing allergens from which essentially all low molecular weight, non-allergenic substances have been removed to react chemically under mild conditions with a solution of an aldehyde in at least two steps, said aldehyde reactions being carried out in a non-phenolic environment, and wherein said mild conditions comprise a reaction step which is carried out using an aldehyde mixture containing a formaldehyde concentration of about 0.36 M to 0.5 M and a lower saturated aliphatic difunctional aldehyde concentration of 0.01 M to 0.1 M at a temperature of from just above the freezing point of the solution to 15° C., and at least one subsequent step which is carried out using a formaldehyde concentration of about 0.06 M to 1.0 M and a lower saturated aliphatic difunctional aldehyde concentration of 0.01 M to 0.1 M at a temperature of from about 25° C. to 40° C., to form a product having intra- or inter-molecular crosslinking induced by said formaldehyde and the allergenic determinant groups are modified to result in substantial reduction of allergenic properties while largely retaining the desired immunizing properties of the native allergen.

48. The product of the process of claim 47.

* * * * *

UNITED STATES PATENT AND TRADEMARK OFFICE
CERTIFICATE OF CORRECTION

PATENT NO. : 4,234,569

DATED : November 18, 1980

INVENTOR(S) : David G. Marsh

It is certified that error appears in the above-identified patent and that said Letters Patent are hereby corrected as shown below:

Insert the following statement immediately following the Abstract:

"The invention described herein was made in the course of work under a grant or award from the Department of Health, Education and Welfare."

Signed and Sealed this

Second Day of February 1982

[SEAL]

Attest:

GERALD J. MOSSINGHOFF

Attesting Officer

Commissioner of Patents and Trademarks